United States Patent
Gomi et al.

(10) Patent No.: US 9,384,494 B2
(45) Date of Patent: Jul. 5, 2016

(54) INFORMATION PROCESSING APPARATUS, INFORMATION PROCESSING METHOD, AND PROGRAM

(71) Applicant: Sony Corporation, Minato-ku (JP)

(72) Inventors: Shinichiro Gomi, Tokyo (JP); Takeshi Koga, Tokyo (JP); Akari Hoshi, Tokyo (JP); Manabu Kii, Tokyo (JP); Ryuichi Namba, Tokyo (JP)

(73) Assignee: Sony Corporation, Minato-ku (JP)

( * ) Notice: Subject to any disclaimer, the term of this patent is extended or adjusted under 35 U.S.C. 154(b) by 122 days.

(21) Appl. No.: 14/147,862

(22) Filed: Jan. 6, 2014

(65) Prior Publication Data

US 2014/0191872 A1 Jul. 10, 2014

(30) Foreign Application Priority Data

Jan. 9, 2013 (JP) ................................. 2013-001873

(51) Int. Cl.
| | |
|---|---|
| G08B 21/00 | (2006.01) |
| G06Q 30/02 | (2012.01) |
| G06Q 50/00 | (2012.01) |
| G06Q 10/08 | (2012.01) |

(52) U.S. Cl.
CPC ........ *G06Q 30/0205* (2013.01); *G06Q 10/0833* (2013.01); *G06Q 30/0201* (2013.01); *G06Q 50/01* (2013.01)

(58) Field of Classification Search
USPC ............................................ 340/539.1, 686.6
See application file for complete search history.

(56) References Cited

U.S. PATENT DOCUMENTS

| | | | | |
|---|---|---|---|---|
| 5,961,332 | A * | 10/1999 | Joao ...................... | G06F 19/363 128/923 |
| 7,801,542 | B1 * | 9/2010 | Stewart .................. | G06Q 50/01 455/414.1 |
| 2001/0040591 | A1 * | 11/2001 | Abbott .................... | G06F 1/163 715/700 |
| 2005/0004923 | A1 * | 1/2005 | Park ....................... | G06Q 30/02 |
| 2007/0179792 | A1 * | 8/2007 | Kramer .................. | G06Q 30/02 705/1.1 |
| 2008/0091515 | A1 * | 4/2008 | Thieberger ........... | G06Q 10/063 705/7.11 |
| 2008/0306826 | A1 * | 12/2008 | Kramer .................. | G06Q 30/02 705/14.14 |
| 2009/0005079 | A1 * | 1/2009 | Shields ............. | G06F 17/30241 455/456.3 |
| 2009/0144635 | A1 * | 6/2009 | Miyazaki .......... | G06F 17/30032 715/747 |
| 2010/0208063 | A1 * | 8/2010 | Lee ..................... | G06K 9/00771 348/143 |
| 2011/0099048 | A1 * | 4/2011 | Weiss ..................... | G06Q 10/00 705/7.34 |

(Continued)

FOREIGN PATENT DOCUMENTS

| | | |
|---|---|---|
| JP | 2005-332309 | 12/2005 |
| JP | 2009-187233 | 8/2009 |

*Primary Examiner* — Jennifer Mehmood
*Assistant Examiner* — Rufus Point
(74) *Attorney, Agent, or Firm* — Chip Law Group

(57) ABSTRACT

There is provided an information processing apparatus including a user state detector configured to detect a state of each of a plurality of users based on sensing data provided from the plurality of users together with position information, a user state integration unit configured to integrate the detected state for each user group defined based on the position information to generate integrated state information, and a state display generator configured to generate information for displaying the integrated state information in association with a position.

19 Claims, 11 Drawing Sheets

(56) References Cited

U.S. PATENT DOCUMENTS

| | | | | |
|---|---|---|---|---|
| 2012/0041825 A1* | 2/2012 | Kasargod | G06Q 30/0272 | 705/14.68 |
| 2012/0290950 A1* | 11/2012 | Rapaport | H04L 51/32 | 715/753 |
| 2012/0311032 A1* | 12/2012 | Murphy | G07F 17/3225 | 709/204 |
| 2013/0059608 A1* | 3/2013 | Cuff | H04W 64/006 | 455/456.5 |
| 2013/0073388 A1* | 3/2013 | Heath | G06Q 50/01 | 705/14.53 |
| 2013/0218967 A1* | 8/2013 | Chau | G06Q 50/01 | 709/204 |
| 2013/0275048 A1* | 10/2013 | Hong | G06F 17/00 | 702/19 |
| 2014/0019867 A1* | 1/2014 | Lehtiniemi | G06Q 50/01 | 715/738 |
| 2014/0095630 A1* | 4/2014 | Wohlert | H04W 4/028 | 709/206 |
| 2014/0250200 A1* | 9/2014 | Geurts | G06Q 50/01 | 709/206 |

* cited by examiner

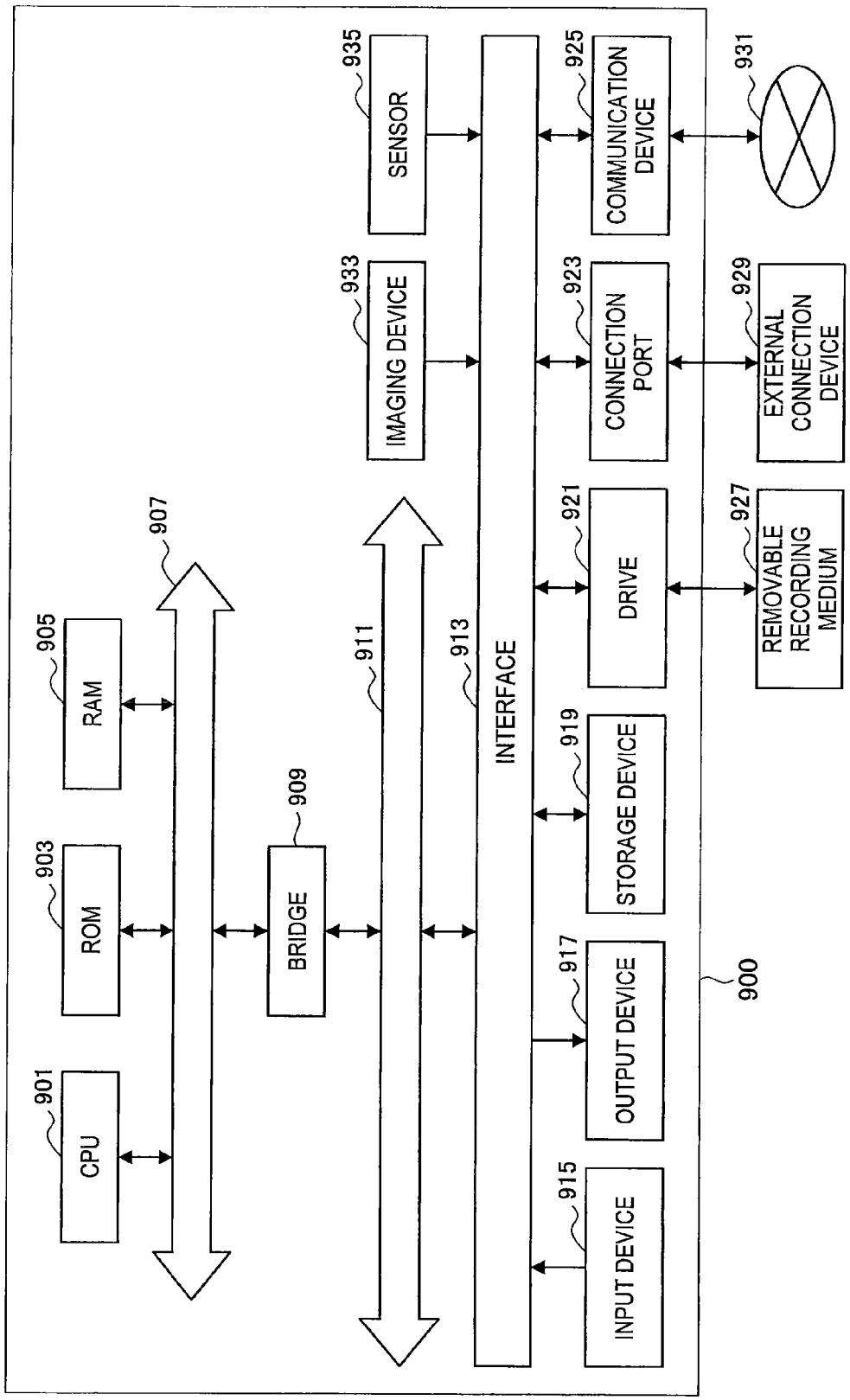

INFORMATION PROCESSING APPARATUS, INFORMATION PROCESSING METHOD, AND PROGRAM

CROSS REFERENCE TO RELATED APPLICATIONS

This application claims the benefit of Japanese Priority Patent Application JP 2013-001873 filed Jan. 9, 2013, the entire contents of which are incorporated herein by reference.

BACKGROUND

The present disclosure relates to an information processing apparatus, an information processing method, and a program.

In recent years, technologies for providing a variety of information to a user based on the user's state that is estimated from the result obtained by sensing biological information or the like of the user have been developed. As an example, a user activity support agent for supporting the subsequent action or behavior of the user based on the user's activity state and its environment situation is disclosed in Japanese Unexamined Patent Application Publication No. 2005-332309. In addition, a technique for displaying an icon that indicates emotion determined based on biological information of the user when taking a photo on a map that represents the shooting position of the photo is disclosed in Japanese Unexamined Patent Application Publication No. 2009-187233.

SUMMARY

For example, with the popularization of services using techniques as described above, data obtained by estimating the state of more users can be provided. However, for example, a technique for integrating and employing information of the state that is estimated for each of a plurality of users has not been proposed. In the related art as disclosed in Japanese Unexamined Patent Application Publication Nos. 2005-332309 and 2009-187233, a user whose state is estimated is the same as a user who is to be provided with information based on the estimated state or only the icon indicating emotion of the user who takes a photo is displayed on the map. For this reason, it is difficult to say that information of the estimated state is integrated and utilized.

Therefore, an embodiment of the present disclosure provides a novel and improved information processing apparatus, information processing method, and program, capable of allowing more useful information to be provided to a user by integrating the state of each user that is detected based on sensing data.

According to an embodiment of the present disclosure, there is provided an information processing apparatus including a user state detector configured to detect a state of each of a plurality of users based on sensing data provided from the plurality of users together with position information, a user state integration unit configured to integrate the detected state for each user group defined based on the position information to generate integrated state information, and a state display generator configured to generate information for displaying the integrated state information in association with a position.

According to an embodiment of the present disclosure, there is provided an information processing method including detecting a state of each of a plurality of users based on sensing data provided from the plurality of users together with position information, integrating the detected state for each user group defined based on the position information to generate integrated state information, and generating information for displaying the integrated state information in association with a position.

According to an embodiment of the present disclosure, there is provided a program for causing a computer to execute detecting a state for each of a plurality of users based on sensing data provided from the plurality of users together with position information, integrating the detected state for each user group defined based on the position information to generate integrated state information, and generating information for displaying the integrated state information in association with a position.

It is possible to achieve, for example, comprehensive recognition of the state of each user at each position by integrating the state of each user detected based on sensing data for each user group defined based on position information of each user. Such comprehensive recognition gives the user a new different perspective from recognizing the state of an individual user, and thus there is a possibility that it effectively supports behavior of the user and leads the user to unexpected discovery.

As described above, according to one or more embodiments of the present disclosure, it is possible to provide information that is more useful to a user by integrating the state of each user that is detected based on sensing data.

BRIEF DESCRIPTION OF THE DRAWINGS

FIG. 11 is a block diagram for explaining a hardware configuration of an information processing apparatus.

DETAILED DESCRIPTION OF THE EMBODIMENT(S)

Figure 1:
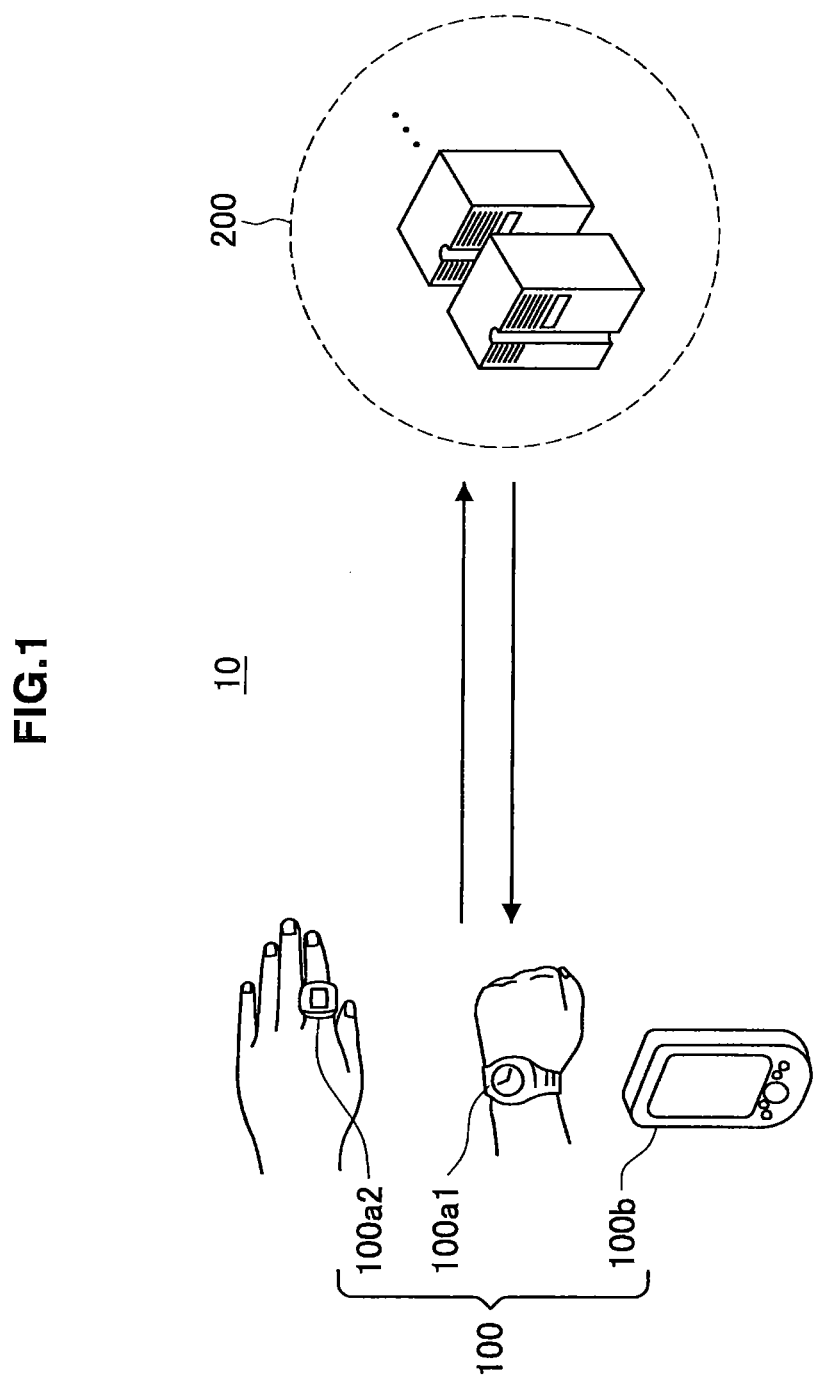
FIG. 1 is a diagram illustrating a schematic configuration of a system according to an embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

A description will be given in the order presented below.
1. Functional Configuration
1-1. Configuration of System
1-2. Configuration of Client
1-3. Configuration of Server
2. Example of Detection of User State
2-1. Detection of Emotion using Pulse
2-2. Detection of Emotion using Brain Waves
2-3. Detection of Emotion using Perspiration
2-4. Other Examples
3. Example of Information to be displayed
3-1. Display of Congestion State on Map
3-2. Display of Emotion on Map
3-3. Display of reflecting User's Preference
3-4. Display in Area within Building
3-5. Display not shown on Map
4. Hardware Configuration
5. Supplement (1. Functional Configuration)

Schematic configurations of a system and a device according to an embodiment of the present disclosure will now be described with reference to FIGS. 1 to 3.

(1-1. Configuration of System)

FIG. 1 is a diagram illustrating a schematic configuration of a system according to an embodiment of the present disclosure. Referring to FIG. 1, the system 10 includes a client 100 and a server 200. The client 100 and the server 200 communicate with each other over a variety of wired or wireless networks. The client 100 includes a sensing terminal 100a and an information display terminal 100b. In the figure, a wristwatch type sensing terminal 100a1 and a ring type sensing terminal 100a2 are illustrated as the sensing terminal 100a.

The sensing terminal 100a acquires information capable of detecting a user's state as sensing data, and transmits it to the server 200 together with position information. The sensing data acquired by the sensing terminal 100a may include, for example, biological information such as a pulse, perspiration, brain waves of the user. The sensing terminal 100a acquires such sensing data, for example, by allowing the sensing terminal 100a to be mounted on a part of the body of the user. A specific shape of the sensing terminal 100a may include, for example, a head mounted display (HMD) type worn on the head, in addition to the wristwatch or ring type illustrated in the figure.

Alternatively, the sensing terminal 100a may acquire, for example, movement history, terminal operation history, or the like of a user as sensing data. In this case, the sensing terminal 100a may be not necessarily a device mounted on a part of the body of the user. The sensing terminal 100a may include, for example, a portable telephone (including smart phone), a tablet or notebook PC (Personal Computer), a portable media player, a portable game machine, or the like, capable of being carried by the user. In this case, the sensing terminal 100a may be the same device as the information display terminal 100b that will be described in detail later. In addition, the sensing terminal 100a and the information display terminal 100b may be implemented as an integrated device capable of acquiring biological information as sensing data, for example, by using a wearable computer.

The server 200 acquires position information and sensing data transmitted from the plurality of sensing terminals 100a. The number of the sensing terminals 100a is not limited to two as illustrated. There may be a plurality of three or more sensing terminals. The server 200 generates information to be displayed by causing the state of each of a plurality of users to be associated with their respective positions in the space at which a position of each of the plurality of users wearing the sensing terminal 100a is defined, based on information acquired from the plurality of sensing terminals 100a. In addition, the server 200 transmits the generated information to the information display terminal 100b.

The information display terminal 100b receives the information transmitted from the server 200 and displays the information to the user. As described above, the information display terminal 100b may be the same device as the sensing terminal 100a, or the information display terminal 100b and the sensing terminal 100a may be implemented as separate devices. As described above, if the information display terminal 100b is the same device as the sensing terminal 100a, the information display terminal 100b may be, for example, a portable telephone (including smart phone), a tablet or notebook PC (Personal Computer), a portable media player, a portable game machine, a wearable computer, or the like. On the other hand, if the information display terminal 100b and the sensing terminal 100a are provided as separate devices, the information display terminal 100b may be any one of described above, or may be a device which is not portable, for example, a desktop PC or a television.

All of the sensing terminal 100a, the information display terminal 100b and the server 200 may be implemented, for example, by the hardware configuration of an information processing apparatus that will be described later. In this case, these devices may be not necessarily implemented by a single information processing apparatus, and further may be implemented, for example, by a plurality of information processing apparatus that cooperate with each other in a state where they are connected with each other via a variety of wired or wireless networks.

(1-2. Configuration of Client)

Figure 2:
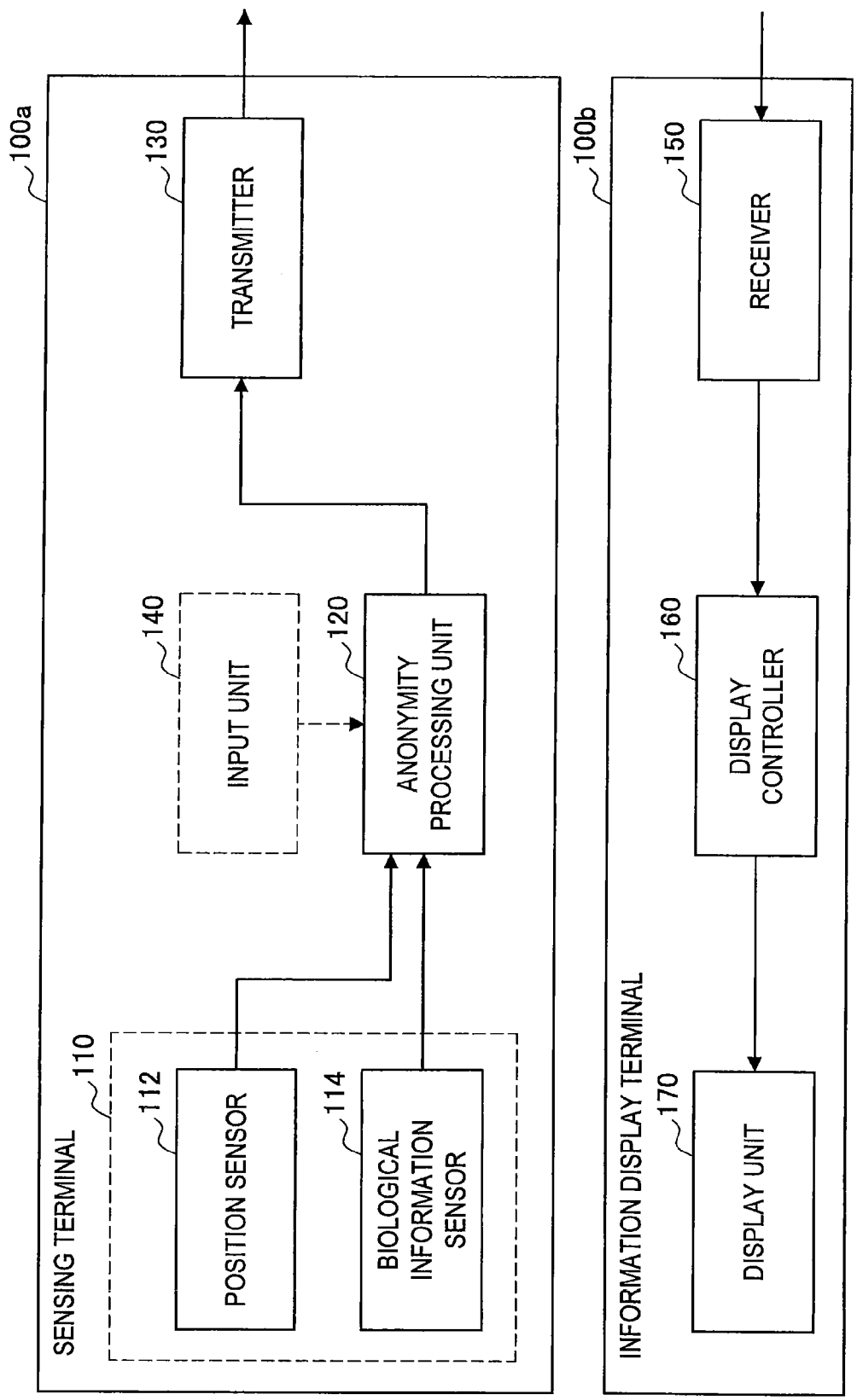
FIG. 2 is a diagram illustrating a schematic functional configuration of a client according to an embodiment of the present disclosure.

FIG. 2 is a diagram illustrating a schematic functional configuration of a client according to an embodiment of the present disclosure. Referring to FIG. 2, the client 100 includes the sensing terminal 100a and the information display terminal 100b. As described above, these terminals may be the same devices or may be separate devices.

(Sensing Terminal)

The sensing terminal 100a includes a sensing unit 110, an anonymity processing unit 120, and a transmitter 130. The sensing terminal 100a may further include an input unit 140.

The sensing unit 110 acquires sensing data and position information to be transmitted to the server 200. The sensing unit 110 includes, for example, a position sensor 112 and a biological information sensor 114. The position sensor 112 detects a position of the sensing terminal 100a (that is, a position of a user), for example, by using a GPS (Global Positioning System) receiver or the like. The position information is used when the server 200 as described above receives the position information and generates information that displays the states of a plurality of users in association with their positions. In addition, the position information may be accumulated as history in the sensing terminal 100a or the server 200 and may be used as sensing data. On the other hand, the biological information sensor 114 may be, for example, a pulsimeter, a perspiration meter, or an electroencephalograph, and acquires biological information of the user, such as a pulse, perspiration, or brain waves. The sensing unit 110 may include, for example, a variety of sensors such as an acceleration sensor, in addition to the sensors described above.

The anonymity processing unit 120 is implemented in software, for example, by using a CPU (Central Processing Unit) or the like. The anonymity processing unit 120 anonymizes the sensing data and position information acquired by the sensing unit 110 upon transmitting them from the transmitter 130 to the server 200. More specifically, the anonymity processing unit 120 assigns an ID which is not related to a user ID or the like to the sensing data and position information. Thus, the server 200 can specify the sensing terminal 100a, but it becomes difficult for the server 200 to specify a user's terminal that is corresponded to the specified sensing terminal 100a.

In the present embodiment, information obtained by integrating sensing data of the user is extracted, and thus sensing data of each user may be provided to the server 200 in a state of being anonymized. As an effect of anonymity, it may become easier for the user to provide personal data such as biological information. In other embodiments, anonymity may be not necessarily performed, and, in this case, the user who provides sensing data may be specified in the server 200. In addition, in a case where information indicating that a user is a child or adult, and male or female is used when the server 200 generates information, the anonymity processing unit 120 may cause these pieces of information to be included in information that is transmitted to the server 200.

The transmitter 130 is implemented as a communication device that communicates with the server 200 via a network. The sensing data and position information acquired by the sensing unit 110 is anonymized in the anonymity processing unit 120, and then the transmitter 130 transmits the anonymized data and information to the server 200.

As an additional configuration, user operation history may be acquired as sensing data by the input unit 140. The input unit 140 is implemented, for example, by a variety of input devices such as a touchpad, a keypad, and a keyboard. The operation history information is provided from the input unit 140 to the anonymity processing unit 120, is anonymized in the anonymity processing unit 120 together with position information, and then is transmitted from the transmitter 130 to the server 200.

(Information Display Terminal)

The information display terminal 100b includes a receiver 150, a display controller 150, and a display unit 170.

The receiver 150 is implemented as a communication device that communicates with the server 200 via a network. The receiver 150 receives information that is generated by the server. This information indicates the state of each user in association with their positions.

The display controller 160 is implemented in software, for example, by using a CPU or the like. The display controller 160 controls the display of the display unit 170 based on information received by the receiver 150. Although not illustrated, the information display terminal 100b may further include an input unit for accepting a user's operation and may change the display of the display unit 17 based on the user's operation. In this case, the information display terminal 100b may transmit a request for new information to the server 200, and the receiver 150 may receive new information transmitted in response to the request. In addition, an example of a display screen of the display unit 170 will be described later.

(1-3. Configuration of Server)

Figure 3:
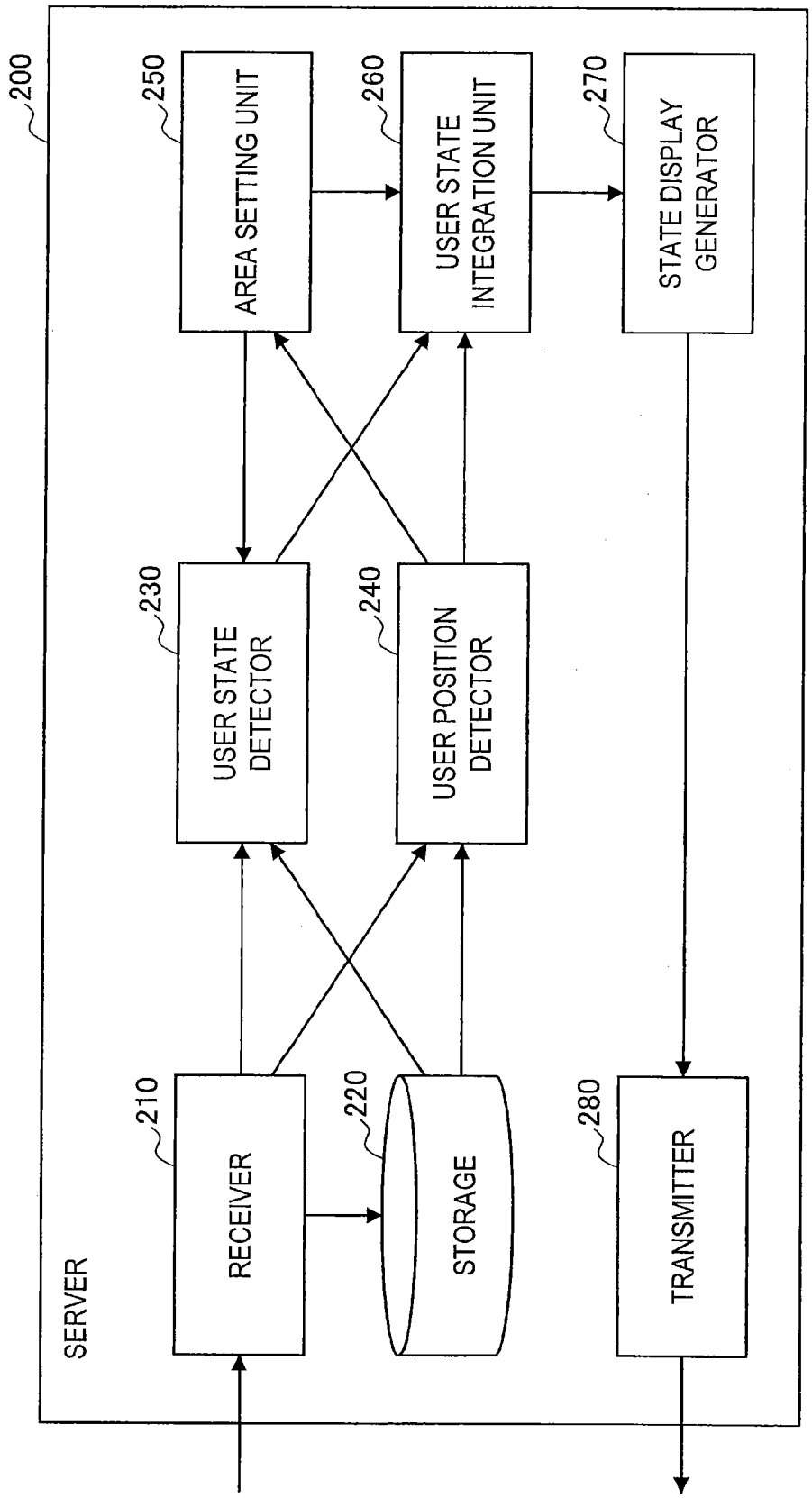
FIG. 3 is a diagram illustrating a schematic functional configuration of a server according to an embodiment of the present disclosure.

FIG. 3 is a diagram illustrating a schematic functional configuration of a server according to an embodiment of the present disclosure. Referring to FIG. 3, the server 200 includes a receiver 210, a storage 220, a user state detector 230, a user position detector 240, an area setting unit 250, a user state integration unit 260, a state display generator 270, and a transmitter 280. The user state detector 230, the user position detector 240, the area setting unit 250, the user state integration unit 260, and the state display generator 270 are implemented, for example, in software by using a CPU or the like.

The receiver 210 is implemented as a communication device that communicates with the sensing terminal 100a via a network. The receiver 210 receives sensing data and position information acquired by the sensing terminal 100a. The receiver 210 may provide these data and information to the user state detector 230 or the user position detector 240 in real time, or may store these data and information in the storage 220 temporarily. The sensing data and position information stored in the storage 220 are read out by the user state detector 230 and the user position detector 240 as necessary.

The user state detector 230 detects the user's state based on the sensing data received by the receiver 210. As described above, the sensing data may be provided from a plurality of users together with position information. The sensing data includes, for example, biological information of the user. The user's state to be detected by the user state detector 230 may indicate, for example, emotion such as excitement, relaxation, joy, anger, sorrow, or pleasure, which is detected based on biological information. The emotion of a user to be detected based on biological information may be detected, for example, as an index value that is represented by a plurality of axes such as an axis including excitement and relaxation and an axis including joy and sorrow. In addition, each emotional state may be detected as separate index values (for example, index value of excitement is set to 80, index value of relaxation is set to 20, index value of joy is set to 60, etc.), and then the user's state may be detected by integrating these index values. Further, the user state detector 230 may detect the congestion state of the user based on position information of the user or may detect an object being concentrated with the users based on terminal operation history of the user. In addition, the user state detector 230 may detect at least one of the illustrated user's states or may detect a plurality of user's states. Further, the user state detector 230, after detecting a plurality of states, may calculate an index value obtained by integrating these states and provide the index value as information indicating the user's state. A specific example of a method of detecting a user's state will be described later.

The user position detector 240 detects the position of a user based on the position information received by the receiver 210. In this regard, the user's position is specifically detected as the position of the sensing terminal 100a. In addition, as described above, in the present embodiment, information transmitted from the sensing terminal 100a is anonymized, and thus the user position detector 240 can specify the relationship between the sensing data and the position information, but the user position detector 240 may not specify a user who provides the information.

The area setting unit 250 sets an area in the space where position information of the user is defined. In the present embodiment, the user's states detected by the user state detector 230 are integrated by a user group in which position information is included in each area which is set by the area setting unit 250. The area to be set by the area setting unit 250 may be, for example, an area on a map, such as an administrative district, a landmark, and so on. In addition, the area to be set by the area setting unit 250 may be, for example, an area which is not necessarily appeared on a map, such as floors in a building, screens in a theater, attractions in an amusement park, and so on. Further, an exemplary display for each setting of an area will be described later.

As other embodiments, the area setting unit 250 may execute a clustering process on position information detected by the user position detector 240 and may define each cluster as an area. In this case, even if an area where the users are gathered is not previously defined in a map, building details, or the like, it is possible to recognize users who are in proximity to each other in position as a user group.

Moreover, the area setting unit 250 may provide information of the set area to the user state detector 230. In this case, the user state detector 230 may recognize a user group that are previously classified by each user, and may change a threshold value for detecting its state for each user group. In this case, for example, the threshold value may be changed depending on the attribute of a location (a location where emotion of a user is easy to change, such as an amusement park or a theater, a location where emotion of a user is difficult to change, such as an office, etc.).

The user state integration unit 260 integrates the user's states detected by the user state detector 230 by each user group defined based on position information to generate integrated state information. The integration of user's state may be achieved by converting information indicating the state of individual user into information (integrated state information) obtained by integrating the user's states belonging to the user group. The information indicating the state of individual user may be, for example, "user A: excitement, user B: excitement, user C: relaxation, user D: excitement, user E: relaxation". The information (integrated state information) obtained by integrating the user's states belonging to the user group may be, for example, "level of excitement of 60%", or "excited user: 3, relaxed user: 2". An example of the integrated state information will be described later.

The state display generator 270 generates information for displaying the integrated state information that is generated by the user state integration unit 260 in association with its position. The state display generator 270 may display the integrated state information, for example, on a map. Alternatively, the state display generator 270 may display the integrated state information in a list that indicates the area. An exemplary display of the integrated state information will be described later.

The transmitter 280 is implemented as a communication device that communicates with the information display terminal 100b via a network. The transmitter 280 transmits the information generated by the state display generator 270 to the information display terminal 100b.

(2. Example of Detection of User State)

An example of detecting user's state in accordance with an embodiment of the present disclosure will be described below.

(2-1. Detection of Emotion using Pulse)

The user state detector 230 can detect excitement or relaxation of the user from the pulse rate of the user that is detected as sensing information, for example, in the following manner. It is known that the pulse rate becomes fast when the user is excited, but the pulse rate becomes slow when the user is relaxed.

(1) Sensing information obtained by detecting a pulse rate $pr_t$ of the user in the sensing terminal 100a is acquired.

(2) A pulse rate $pf_t$ obtained by filtering the detected pulse rate $pr_t$ is acquired by using any one of the following Equations (1) to (3). In the following Equations, K is an optional parameter, and median represents a function that calculates a median value.

$$pf_t = \sum_{i=t-n}^{t} pr_i \quad (1)$$

$$pf_t = pr_t - K(pr_t - pf_{t-1}) \quad (2)$$

$$pf_t = \text{median}(pr_{t-n}, \ldots, pr_{t-1}, pr_t) \quad (3)$$

(3) As described below, an emotion of the user is estimated based on the result obtained by comparing a threshold value $p_{thresh1}$ and threshold value $p_{thresh2}$ with a value $(pf_t - p_{ave})/\sigma$ produced by dividing the difference between the filtered pulse rate $pf_t$ and its average value $p_{ave}$ by the variance.

$(pf_t - p_{ave})/\sigma > p_{thresh1}$: It is estimated that the user is in an excited state $(pf_t - p_{ave})/\sigma < -p_{thresh2}$: It is estimated that the user is in a relaxed state Otherwise: It is estimated that the user is in a normal state The average value $p_{ave}$ and the variance $\sigma$ may be an average value and the variance, respectively, of the user to be estimated, or may be an average value and the variance, respectively, of the entire user including other users. The threshold value $p_{thresh1}$ and the threshold value $p_{thresh2}$ are optionally set, and as an example, may be set to $0.8\sigma$. As described above, the threshold values may be set to different values for each user group.

(2-2. Detection of Emotion using Brain Waves)

The user state detector 230, for example as described below, can detect excitement or relaxation of the user from intensity of brain waves of the user that is detected as sensing information. It is known that an intensity of alpha waves of brain waves indicates the degree of relaxation, and an intensity of beta waves thereof indicates the degree of excitement.

(1) In the sensing terminal 100a, sensing information obtained by detecting the intensity of alpha waves $\alpha f_t$ and the intensity of beta waves $\beta r_t$ of brain waves of the user is acquired.

(2) For example using any one of the following Equations (4) to (6), an intensity of alpha waves $\alpha f_t$ and an intensity of beta waves $\beta f_t$ are acquired by filtering the detected intensity of alpha waves $\alpha r_t$ and intensity of beta waves $\beta r_t$, respectively. In the following Equations, K is an optional parameter, and median represents a function that calculates a median value.

$$\alpha f_t = \sum_{i=t-n}^{t} \alpha r_i, \, \beta f_t = \sum_{i=t-n}^{t} \beta r_i \quad (4)$$

$$\alpha f_t = \alpha r_t - K(\alpha r_t - \alpha f_{t-1}), \quad (5)$$
$$\beta f_t = \beta r_t - K(\beta r_t - \beta f_{t-1})$$

$$\alpha f_t = \text{median}(\alpha r_{t-n}, \ldots, \alpha r_{t-1}, \alpha r_t) \quad (6)$$
$$\beta f_t = \text{median}(\beta r_{t-n}, \ldots, \beta r_{t-1}, \beta r_t)$$

As described below, an emotion of the user is estimated based on the result obtained by comparing a threshold value $\alpha_{thresh}$ and threshold value $\beta_{thresh}$ with values $(\alpha f_t - \alpha_{ave})/\sigma_\alpha$ and $(\beta f_t - \beta_{ave})/\sigma_\beta$, respectively, produced by dividing the difference between the filtered intensity of alpha waves $\alpha f_t$ and intensity of beta waves $\beta f_t$ and their respective average values $\alpha_{ave}$ and $\beta_{ave}$ by the respective variances.

$(\beta f_t - \beta_{ave})/\sigma_\beta > \beta_{thresh}$: It is estimated that the user is in an excited state $(\alpha f_t - \alpha_{ave})/\sigma_\alpha > \alpha_{thresh}$: It is estimated that the user is in a relaxed state Otherwise: It is estimated that the user is in a normal state The average values $\alpha_{ave}$ and $\beta_{ave}$ and the variances $\sigma_\alpha$ and $\sigma_\beta$ may be average values and variances, respectively, of the user to be estimated, or may be average values and variances, respectively, of the entire user including other users. The threshold values $\alpha_{thresh}$ and $\beta_{thresh}$ are optionally set, and as an example, may be set to 0.80 $\sigma_\alpha$ and 0.8 $\sigma_\beta$, respectively. As described above, the threshold values may be set to different values for each user group.

(2-3. Detection of Emotion using Perspiration)

The user state detector 230, for example as described below, can detect excitement or relaxation of the user from a perspiration amount of the user that is detected as sensing information. It is known that the perspiration amount increases as the user is excited, and the perspiration amount decreases as the user is relaxed.

(1) In the sensing terminal 100*a*, sensing information obtained by detecting the perspiration amount $s_t$ of the user is acquired.

(2) Using any one of the following Equations (7) to (9), a perspiration amount $sf_t$ obtained by filtering the detected perspiration amount $s_t$ is acquired. In the following Equations, K is an optional parameter, and median represents a function that calculates a median value.

$$sf_t = \sum_{i=t-n}^{t} s_i \quad (7)$$

$$sf_t = s_t - K(s_t - sf_{t-1}) \quad (8)$$

$$sf_t = \text{median}(s_{t-n}, \ldots, s_{t-1}, s_t) \quad (9)$$

(3) As described below, an emotion of the user is estimated based on the result obtained by comparing a threshold value $s_{thresh1}$ and threshold value $s_{thresh2}$ with a value $(sf_t - s_{ave})/\sigma$ produced by dividing the difference between the filtered perspiration amount $sf_t$ and its average value $s_{ave}$ by the variance.

$(sf_t - s_{ave})/\sigma > s_{thresh1}$: It is estimated that the user is in an excited state $(sf_t - s_{ave})/\sigma < -s_{thresh2}$: It is estimated that the user is in a relaxed state Otherwise: It is estimated that the user is in a normal state The average value $s_{ave}$ and the variance $\sigma$ may be an average value and variance, respectively, of the user to be estimated, or may be an average value and variance, respectively, of the entire user including other users. The threshold value $s_{thresh1}$ and threshold value $s_{thresh2}$ are optionally set, and as an example, may be set to $0.8\sigma$. As described above, the threshold values may be set to different values for each user group.

(2-4. Other Examples)

As described above, as sensing information, history of position information provided from the sensing terminal 100*a* can be used. In this case, for example, if the number of users who are in proximity to each other in position is equal to or greater than a predetermined number, it can be estimated to be in a state where these users are concentrated. For example, when users included in a user group are in a state where they are concentrated, the user state integration unit 260 may generate integrated state information indicating that the users are gathered in an area corresponding to the user group.

Furthermore, terminal operation history of the sensing terminal 100*a* can be used as sensing information. In this case, for example, if a terminal operation of a user is frequently performed, it is estimated to be in a state where users is focused on operation of a terminal other than what is happening at the place. For example, if the terminal operation of a user in a stadium is frequently performed, it is estimated that the user is not focused on a match. If the proportion of users who is not focused on the match among the users in the stadium is high, the user state integration unit 260 may generate information indicating, "user (watching the match) is not excited" as integrated state information.

In addition, a technique that estimates a state indicating user's emotion or the like using various technologies has been proposed. In an embodiment of the present disclosure, it is possible to detect user's state from sensing information by allowing the user state detector 230 to employ appropriately such a technique.

(3. Example of Information to be Displayed)

An example of information to be displayed in accordance with an embodiment of the present disclosure will now be described with reference to FIGS. 4 to 10.

(3-1. Display of Congestion State on Map)

Figure 4:
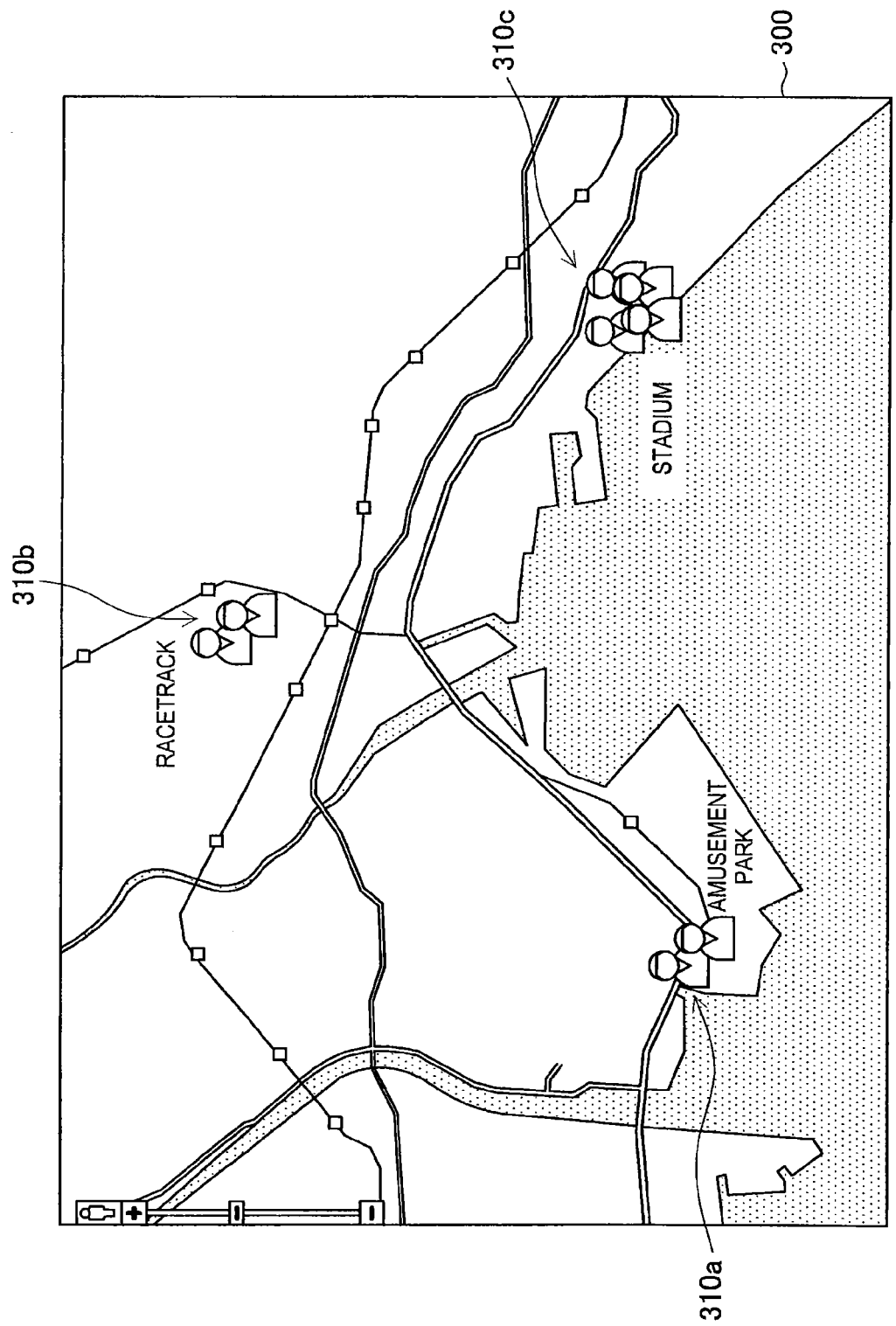
FIG. 4 is a diagram illustrating an example of displaying a congestion state of users on a map in accordance with an embodiment of the present disclosure.

FIG. 4 is a diagram illustrating an example of displaying a congestion state of a user on a map in accordance with an embodiment of the present disclosure. Referring to FIG. 4, an icon 310 indicating users who are in a congestion state is displayed on a map 300. The icon 310 includes an icon 310*a* indicating users who are concentrated in an amusement park, an icon 310*b* indicating users who are concentrated in a racetrack, and an icon 310*c* indicating users who are concentrated in a stadium.

In the example illustrated, if the number of users who are in proximity to each other in position is greater than a predetermined number, the user state detector 230 estimates that these users are in a state where they are concentrated. For example, the distance used to determine the proximity may be set optionally, and for example, may be set based on the size of an amusement park, a racetrack, a stadium, or the like that is a facility where common people gather.

Furthermore, the number of the icons 310 may represent the number of users who are in a congestion state. In the example illustrated, two icons 310*a*, two icons 310*b*, and four icons 310*c* are displayed. For example, if it is assumed that these icons are proportional in number to users who are in a congestion state, it can be found that the number of users concentrated in the amusement park is substantially same as that of users concentrated in the racetrack, and the number of users concentrated in the stadium is twice as many as the number of users concentrated in the amusement park or the racetrack.

As another example, the icon 310 may represent the number of users by means of color or shape. For example, the color of the icon 310 may be displayed in white color when the number of users is small, and then may be displayed in red color gradually with increasing the number of users. Alternatively, the icon 310 may be displayed in a size corresponding to the number of users.

In the above example, the congestion state of users is automatically detected, and thus it is recognized that users are concentrated, for example, even in a place other than a landmark (for example, racetrack, stadium, etc.) that has been registered in advance. Therefore, for example, even when users are concentrated due to an unexpected event or something being held on the street, it is possible to detect the congestion and thus it can lead a user who wants to participate in the event to the place.

(3-2. Display of Emotion on Map)

Figure 5:
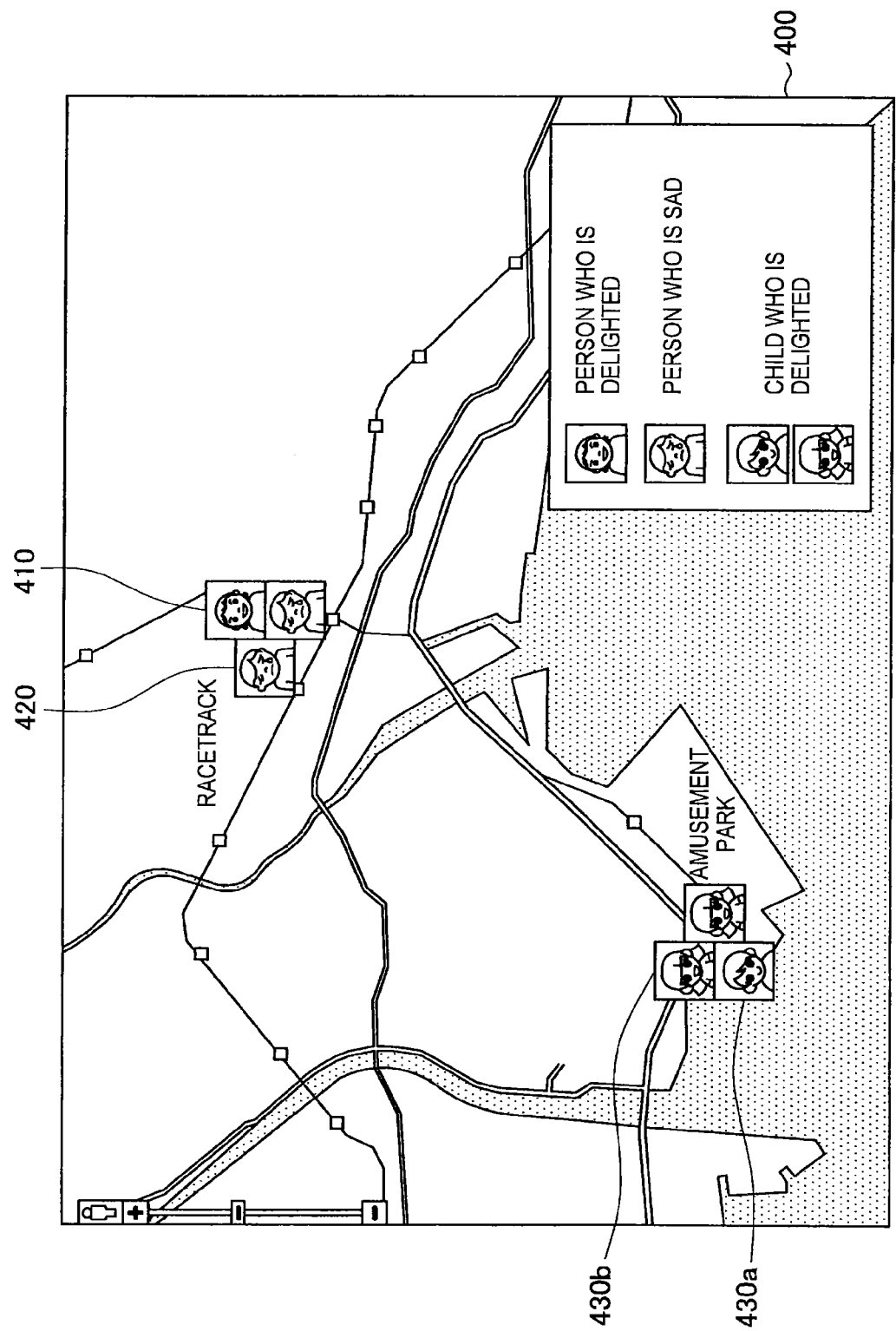
FIG. 5 is a diagram illustrating an example of displaying emotions of a user on a map in accordance with an embodiment of the present disclosure.

FIG. 5 is a diagram illustrating an example of displaying emotions of a user on a map in accordance with an embodiment of the present disclosure. Referring to FIG. 5, icons 410, 420, and 430 that indicate the emotions of users in their respective places are displayed on a map 400. The icon 410 indicates a person (adult) who is delighted, the icon 420 indicates a person (adult) who is sad, and the icon 430 indicates a child who is delighted. The icon 430 includes an icon 430a that indicates a boy and an icon 430b that indicates a girl.

In the example illustrated, the user state detector 230 estimates whether the user is delighted or sad, for example, based on the detection of excitement or relaxation described above, the intensity of movement of the user detected by an acceleration sensor, or the like. For example, if a user is excited and its movement is intense, then it may be estimated that the user is delighted. In addition, if a user is relaxed, or the user is excited but the user's movement is small, then it may be estimated that the user is sad. The determination of whether the user is an adult or child may be made, for example, based on information of user registered in advance.

Furthermore, in the above example, the user state integration unit 260 and the state display generator 270 determine the number of users who are delighted or sad, or who are an adult or child among users in a given area (in the above example, an amusement park or a racetrack). If the number of users according to the respective classifications exceeds a predetermined number, icons 410, 420, and 430 indicating emotions of the user are displayed on corresponding respective areas. In this case, the icons 410, 420, and 430 may represent the number of users who are in the respective states by means of number, color, or shape.

In this example, it is recognized what types of emotions a user feels in each place. Further, additionally, it is recognized whether the user who is delighted or sad in each place is an adult or child. In that reason, the information to be provided may be effective, for example, to assist the behavior of the user who is looking for the place where the user wants to go. In the case of the illustrated example, a user with a child can choose an amusement park where many children are delighted as the place where the user wants to go. In addition, an adult user who wants to get some stimulation can choose a racetrack where adults have mingled feelings of joy and sorrow as the place where the user wants to go.

Figure 6:
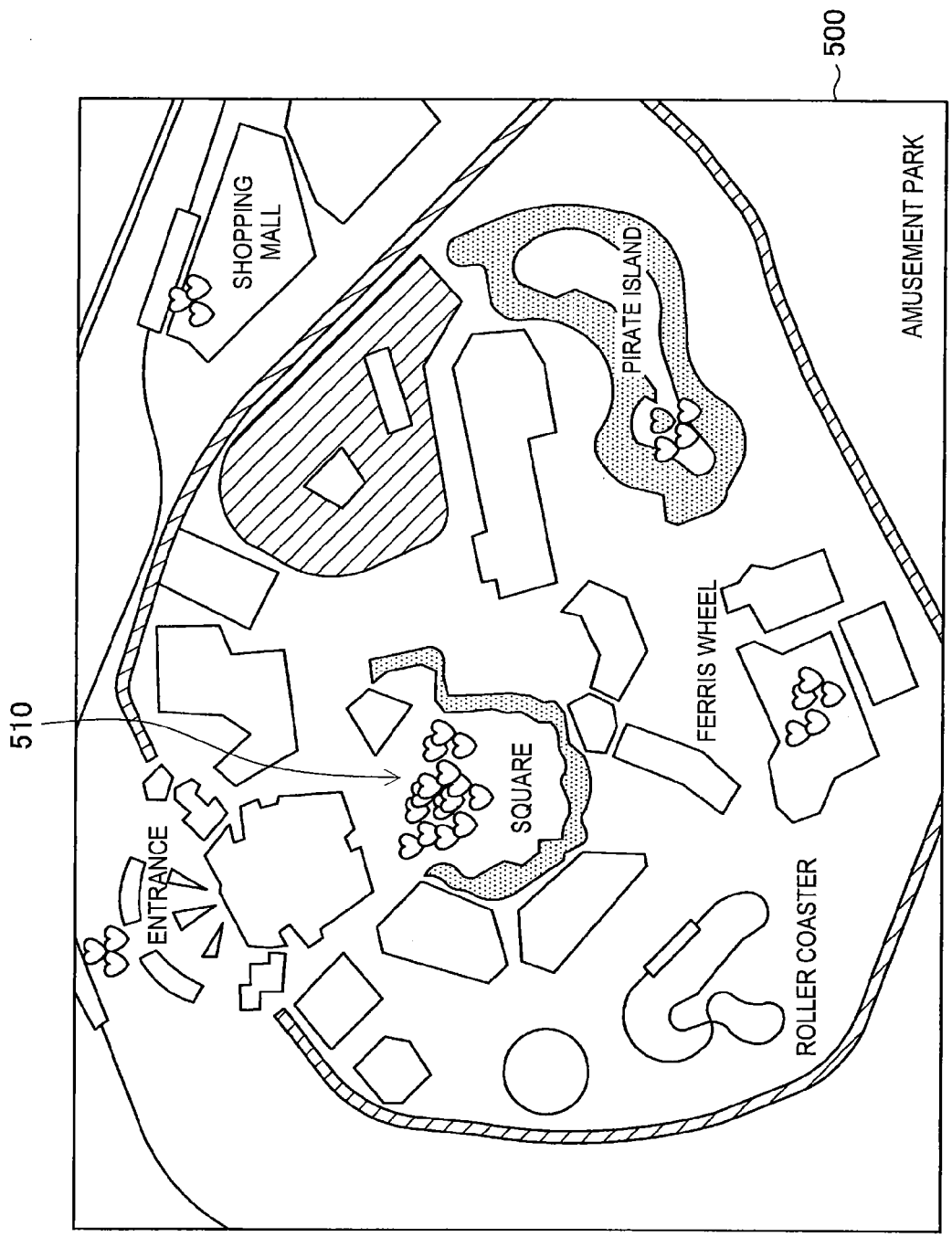
FIG. 6 is a diagram illustrating an example of displaying emotions of a user on an enlarged map in accordance with an embodiment of the present disclosure.

FIG. 6 is a diagram illustrating an example of displaying emotions of a user on an enlarged map in accordance with an embodiment of the present disclosure. Referring to FIG. 6, an icon 510 indicating users who are delighted at different places (square, entrance, and attractions) is displayed on an enlarged map 500 of an amusement park. The enlarged map 500 may be displayed, for example, when the amusement park is selected or enlarged in the map 400 represented by the example of FIG. 5.

The enlarged map 500 is different from the map 400 in that only one type of the icon 510 is displayed on the enlarged map 500. This is because the necessity of displaying a user who is sad is relatively low due to features of the place of the amusement park. Thus, when the place to be displayed is narrowed (or when the place has been narrowed for the beginning), the user state detector 230 and the user state integration unit 260 may change the type of the user's state to be detected or displayed depending on features of the place.

The icon 510 is displayed in a heart shape and represents the number of users who are delighted by the number of the icon 510. The icon 510 may represent that one user is delighted, and may represent that a predetermined number of two or more users are delighted. However, it is not limited to this example; the icon 510 may be, for example, an icon representing a facial expression of the user in a similar way to the icon 430 of the example shown in FIG. 5. In addition, the icon 510 may represent the number of users who are delighted by means of color or shape.

The distribution of the icons 510 does not necessarily coincide with that of the entire user. The distribution of the icons 510 coincides with that of users who are delighted among users. Thus, for example, even though a roller coaster is crowded with many users, the icons 510 may not be distributed in the roller coaster. In this case, the roller coaster may be newly built and many users be gathered, but it may be actually a disappointing attraction. In such a case, not only the number of other users, but also the icon 510 that is information representing its state is displayed. This is useful in that it allows users to be more reliably attracted to an enjoyable place.

(3-3. Display of reflecting User's Preference)

Figure 7:
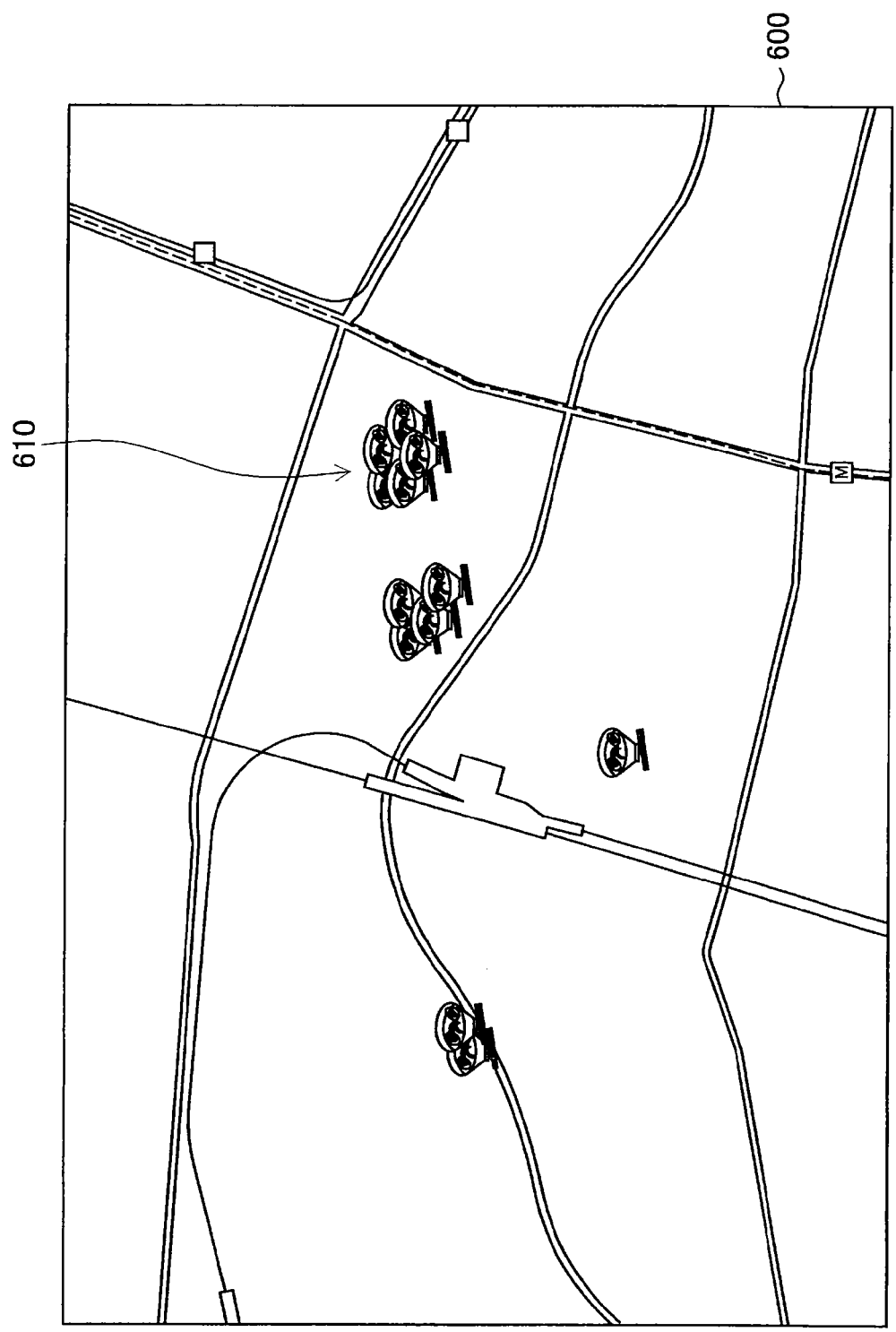
FIG. 7 is a diagram illustrating an example of reflecting an attribute of a user in a display on a map in accordance with an embodiment of the present disclosure.

FIG. 7 is a diagram illustrating an example of reflecting an attribute of a user in a display on a map in accordance with an embodiment of the present disclosure. Referring to FIG. 7, an icon 610 representing ramen (noodle soup dish) is displayed on a map 600. The icon 610 is displayed, for example, when a state where a user located in a ramen shop registered in advance is excited is detected. Alternatively, the icon 610 may be displayed, when a predetermined number or more of users who registered in advance that they had a preference for ramen are gathered and excited.

This display makes it possible for the user to know that there is a ramen shop having a good reputation in a place where the icon 610 is displayed. For example, it is easy to cause the registered ramen shop to be displayed on the map, but in this case, it is not easy to know whether the ramen shop has a good reputation or not. However, the icon 610 represents the ramen shop where users are actually excited, and thus it may be effective, for example, to assist the behavior of the user who is looking for a ramen shop in an unfamiliar place.

Figure 8:
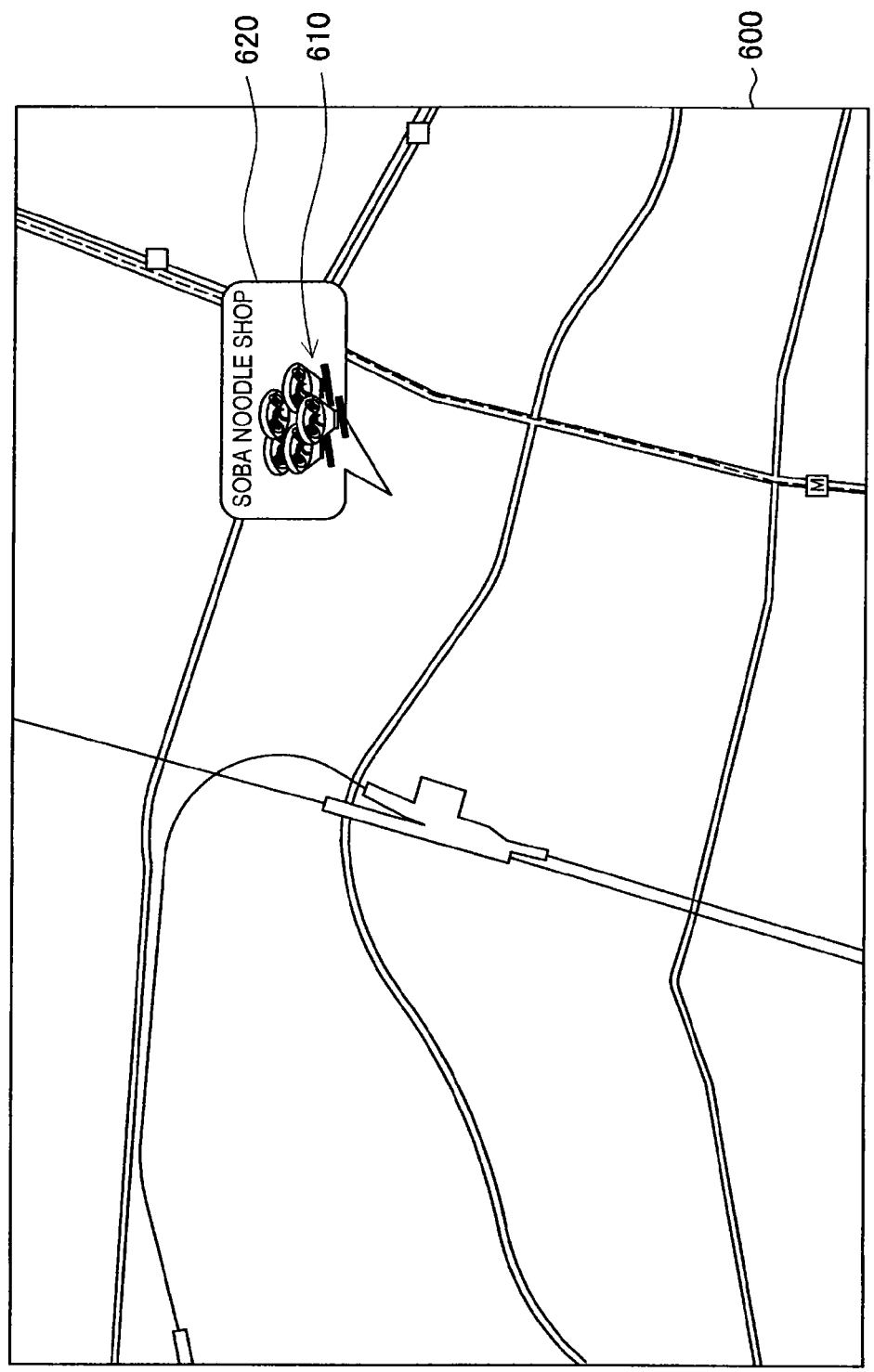
FIG. 8 is a diagram illustrating an example of selecting any one place in the example of FIG. 7.

FIG. 8 is a diagram illustrating an example of selecting any one place in the example of FIG. 7. Referring to FIG. 8, in a pop-up 620 representing information related to the selected place, an icon 610 represented in that place is displayed. The display of the pop-up 620 makes it possible for the user to obtain detailed information of the place where the icon 610 is displayed.

The icon 610 displayed in this example is displayed in the case of the latter example of FIG. 7 described above, that is, when a predetermined number or more of users who registered in advance that they had a preference for ramen are gathered and excited. Thus, the place where the icon 610 is displayed is not necessarily limited to the ramen shop. In the illustrated example, information of a soba noodle shop as the pop-up 620 is displayed, it is found that the place where the icon 610 is displayed is the soba noodle shop. Soba noodles are noodles different in type from ramen. In this case, there is a possibility that the user makes an expected discovery, "a soba noodle shop where lovers of ramen are gathered".

The display as illustrated in the example of FIG. 7 or FIG. 8 described above is displayed, for example, based on the user's preference that is estimated from the place where each user registers in advance or the user is located. In a case where it is necessary to perform such a display in the information display terminal 100b, for example, the user explicitly enters a ramen shop to be sought, and may request that the information display terminal 100b allows the server 200 to filter information to be displayed by a preference, "liking for ramen".

In this case, for example, the user state integration unit 260 extracts a user (user group corresponding to an area having a predetermined attribute) who is located in a ramen shop or a user (user having a predetermined attribute from among users included in a user group) who registers in advance a preference for ramen from among users who are in an excited state, which are detected by the user state detector 230. Then, the user state integration unit 260 generates integrated state information for the extracted user. For example, if a user who wants to refer information from the information display terminal 100b previously registers a preference for ramen, or if it is estimated that the user prefers ramen from information search history or the like of the user, the filtering similar to that described above may be performed automatically.

(3-4. Display in Area within Building)

Figure 9:
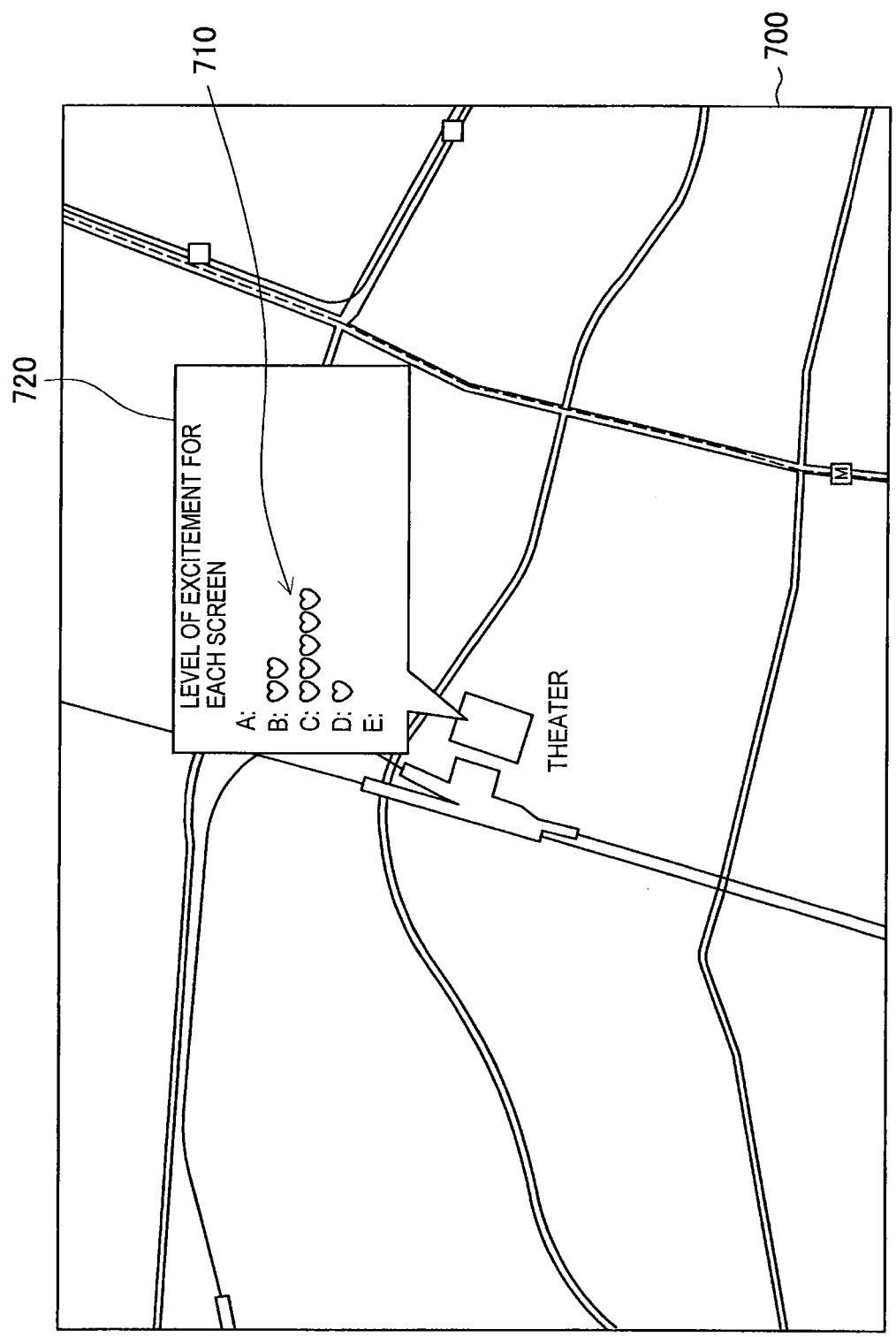
FIG. 9 is a diagram illustrating an example of displaying the state of a user for an area within a building in accordance with an embodiment of the present disclosure.

FIG. 9 is a diagram illustrating an example of displaying the state of a user in an area within a building in accordance with an embodiment of the present disclosure. Referring to FIG. 9, a pop-up 720 is displayed at a theater on a map 700 and the number of users who are excited at each screen of the theater is displayed in the pop-up 720 as "level of excitement" by using an icon 710.

Even in the building, for example by allowing the sensing terminal 100a to obtain position information of a wireless base station for receiving a radio wave, the position information can be obtained in units of floors or rooms. In this case, it is possible to define a user group for each area in the building. In the illustrated example, by applying this to the theater, the screens (projection rooms) showing different movies are set as respective areas, and the "level of excitement" is displayed on each screen. The information provided in this way may be effective, for example, to assist the behavior of the user to select a movie to watch. The icon 710 is displayed in a similar way to the icon 510 in the example of FIG. 6 except that the icon 710 is displayed on a list of screens, and thus a detailed description thereof is omitted.

(3-5. Display not Shown on Map)

Figure 10:
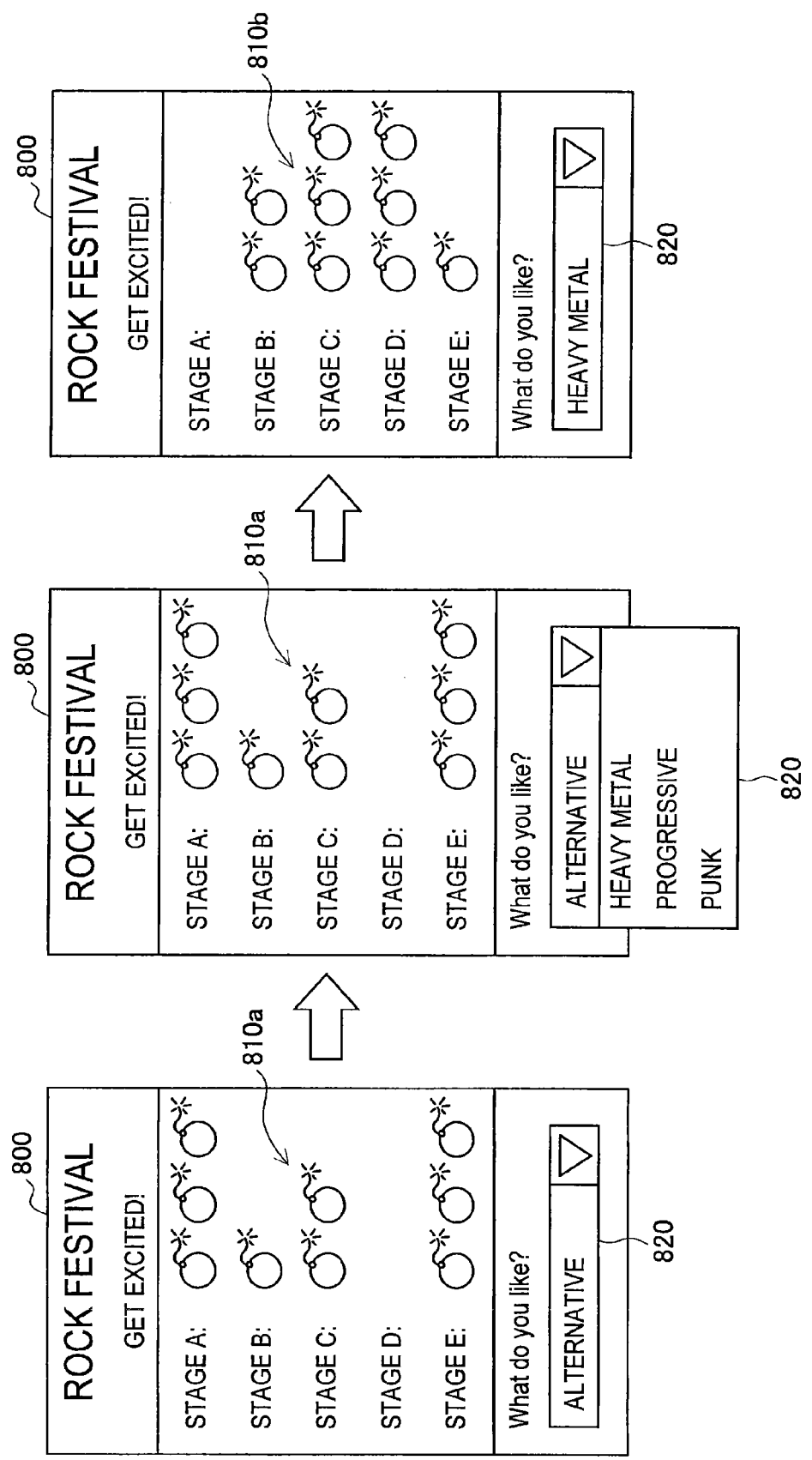
FIG. 10 is a diagram illustrating an example in which display is not shown on a map in accordance with an embodiment of the present disclosure.

FIG. 10 is a diagram illustrating an example in which display is not shown on a map in accordance with an embodiment of the present disclosure. Referring to FIG. 10, an icon 810 and a preference selection indication 820 are displayed on a screen 800. The screen 800 displays the level of excitement for each stage of a rock festival in which performances are playing at a plurality of stages.

The icon 810 indicates the number or proportion of users who are excited from among users located in an area of each stage (A to E). When the icon 810 is displayed, the filtering is implemented by the preference of the user selected by the preference selection indication 820.

For example, when "ALTERNATIVE" is selected by the preference selection indication 820, the user state integration unit 260 calculates the level of excitement for the user who registers "ALTERNATIVE" as a preference of music, and as a result, a icon 810a is displayed. The icon 810a indicates that the level of excitement in the stages A and E is high.

On the other hand, when "HEAVY METAL" is selected by the preference selection indication 820, the user state integration unit 260 recalculates the level of excitement for the user who registers "HEAVY METAL" as a preference of music, and as a result, a icon 810b is displayed. The icon 810b indicates that the level of excitement in the stages C and D is high, which is different from the icon 810a.

In this example, the icon 810 is not displayed on a map but it is displayed in the list of areas (stages). In this way, in the embodiments of the present disclosure, the display indicating the user's state may be not necessarily displayed on a map. In addition, the user state integration unit 260 calculates the level of excitement by filtering the user based on the user's preference which is selected by the preference selection indication 820, and thus it is possible to induce a user to an area (stage) where other users having a similar preference to that of the user are excited.

(4. Hardware Configuration)

A hardware configuration of the information processing apparatus according to the embodiment of the present disclosure will be described with reference to FIG. 11. FIG. 11 is a block diagram for explaining a hardware configuration of the information processing apparatus. The illustrated information processing apparatus 900 may be implemented as a client (the sensing terminal and the information display terminal) and a server in the embodiments described above, for example.

The information processing apparatus 900 includes a CPU (Central Processing Unit) 901, a ROM (Read Only Memory) 903, and a RAM (Random Access Memory) 905. In addition, the information processing apparatus 900 may include a host bus 907, a bridge 909, an external bus 911, an interface 913, an input device 915, an output device 917, a storage device 919, a drive 921, a connection port 923, and a communication device 925. Further, the information processing apparatus 900 may include an imaging device 933 and a sensor 935 as necessary. The information processing apparatus 900 may include a processing circuit such as a DSP (Digital Signal Processor), alternatively or in addition to the CPU 901.

The CPU 901 serves as an operation processor and a controller, and controls all or some operations in the information processing apparatus 900 in accordance with various programs recorded in the ROM 903, the RAM 905, the storage device 919, or a removable recording medium 927. The ROM 903 stores programs and operation parameters that are used by the CPU 901. The RAM 905 primarily stores programs that are used in the execution of the CPU 901 and parameters that are appropriately modified in the execution. The CPU 901, ROM 903, and RAM 905 are connected to each other by the host bus 907 configured to include an internal bus such as a CPU bus. In addition, the host bus 907 is connected to the external bus 911 such as a PCI (Peripheral Component Interconnect/Interface) bus via the bridge 909.

The input device 915 may be a device that is operated by a user, such as a mouse, a keyboard, a touch panel, buttons, switches, and a lever. The input device 915 may be, for example, a remote control unit using infrared light or other radio waves, or may be an external connection device 929 such as a portable phone operable in response to the operation of the information processing apparatus 900. Furthermore, the input device 915 includes an input control circuit configured to generate an input signal based on information that is inputted by a user and output the generated input signal to the CPU 901. By operating the input device 915, a user can input various types of data to the information processing apparatus 900 or issue instructions for causing the information processing apparatus 900 to perform a processing operation.

The output device 917 includes a device that notifies the acquired information visually or audibly to a user. The output device 917 may include a display device such as LCD (Liquid Crystal Display), PDP (Plasma Display Panel), and organic EL (Electro-Luminescence) displays, an audio output device such as speaker and headphone, and a peripheral device such as printer. The output device 917 may output the results obtained from the process of the information processing apparatus 900 in a form of a video such as text or image and an audio such as voice or sound.

The storage device 919 is a data storage device that is configured as an example of a storage unit of the information processing apparatus 900. The storage device 919 includes, for example, a magnetic storage device such as HDD (Hard Disk Drive), a semiconductor storage device, an optical storage device, or a magneto-optical storage device. The storage device 919 stores programs to be executed by the CPU 901, various data, and data obtained from the outside.

The drive 921 is a reader/writer for the removable recording medium 927 such as a magnetic disk, an optical disk, a magneto-optical disk, or a semiconductor memory, and is embedded in the information processing apparatus 900 or attached externally thereto. The drive 921 reads information recorded in the removable recording medium 927 attached thereto, and outputs the read information to the RAM 905. Further, the drive 921 can write records in the removable recording medium 927 attached thereto.

The connection port 923 is a port used to directly connect devices to the information processing apparatus 900. The connection port 923 may include a USB (Universal Serial Bus) port, an IEEE1394 port, and a SCSI (Small Computer System Interface) port. The connection port 923 may further include an RS-232C port, an optical audio terminal, an HDMI (High-Definition Multimedia Interface) port, and so on. The connection of the external connection device 929 to the connection port 923 makes it possible to exchange various data between the information processing apparatus 900 and the external connection device 929.

The communication device 925 is, for example, a communication interface including a communication device or the like for connection to a communication network 931. The communication device 925 may be, for example, a communication card for a wired or wireless LAN (Local Area Network), Bluetooth (registered trademark), WUSB (Wireless USB) or the like. In addition, the communication device 925 may be a router for optical communication, a router for ADSL (Asymmetric Digital Subscriber Line), a modem for various kinds of communications, or the like. The communication device 925 can transmit and receive signals to and from, for example, Internet, or other communication devices based on a predetermined protocol such as TCP/IP. In addition, the communication network 931 connected to the communication device 925 may be a network or the like connected in a wired or wireless manner, and may be, for example, Internet, a home LAN, infrared communication, radio wave communication, satellite communication, or the like.

The imaging device 933 is a device that generates an image by imaging a real space using an image sensor such as a charge-coupled device (CCD) or complementary metal-oxide-semiconductor (CMOS) sensor, as well as various members such as one or more lenses for controlling the formation of a subject image on the image sensor, for example. The imaging device 933 may be a device that takes still images, or alternatively or in addition, the imaging device 933 may be a device that takes moving images.

The sensor 935 is any of various sensors such as an acceleration sensor, a gyro sensor, a geomagnetic sensor, an optical sensor, or a sound sensor, for example. The sensor 935 acquires information regarding the state of the information processing apparatus 900 itself, such as the orientation of the housing of the information processing apparatus 900 and information regarding the environment surrounding the information processing apparatus 900, such as the brightness or noise surrounding the information processing apparatus 900. The sensor 935 may also include a Global Positioning System (GPS) sensor that receives GPS signals and measures the latitude, longitude, and altitude of the apparatus.

In the above, an exemplary hardware configuration of the information processing apparatus 900 has been illustrated. Each of the above components may be configured using general-purpose members, or may be configured by a hardware specialized in the function of each component. Such a configuration may be modified as appropriate according to the technological level at the time of the implementation.

(5. Supplement)

Embodiments of the present disclosure encompass an information processing apparatus (a client or a server) and system as described in the foregoing, an information processing method executed by an information processing apparatus or system, a program for causing an information processing apparatus to function, and a non-transitory tangible medium storing such a program, for example.

In the above embodiments, both of what is displayed on the map and what is not displayed on the map are included, and the integrated state information is generated based on position information defined in real space, but the exemplary implementation of the present disclosure is not limited to these embodiments. For example, the integrated state information may be generated based on position information defined in virtual space. As an example, an upsurge of the battle in each area of a field may be presented to players of a group battle game in the field set in virtual space by the level of excitement of other users who are participating.

Furthermore, in the above embodiments, a user group is defined for each of relative large areas such as an area on a map and a floor or room of a building, but the exemplary implementation of the present disclosure is not limited to these embodiments. For example, the user group may be defined for each area that is set in the room. As an example, the user group may be defined for each area of each department in the office. In this case, the sensing terminal may be a PC used by each user, and the position information may be obtained from a network address assigned to the PC. For example, in some industries, it is possible to grasp whether staffs in each department are diligent or not as a whole, by obtaining operation history of the PC as sensing information.

Although preferred embodiments of the present disclosure are described in detail with reference to the accompanying drawings, the technical scope of the present disclosure is not limited thereto. It should be understood by those skilled in the art that various modifications, combinations, sub-combinations and alterations may occur depending on design requirements and other factors insofar as they are within the scope of the appended claims or the equivalents thereof.

Additionally, the present technology may also be configured as below.

(1) An information processing apparatus including:
  a user state detector configured to detect a state of each of a plurality of users based on sensing data provided from the plurality of users together with position information;
  a user state integration unit configured to integrate the detected state for each user group defined based on the position information to generate integrated state information; and
  a state display generator configured to generate information for displaying the integrated state information in association with a position.

(2) The information processing apparatus according to (1),
  wherein the user state detector detects a state of each of the plurality of users based on the sensing data including biological information of each of the plurality of users.

(3) The information processing apparatus according to (2),
  wherein the user state detector detects a state of each of the plurality of users by comparing a numerical value based on the biological information with a threshold value.

(4) The information processing apparatus according to (3),
  wherein the user state detector sets the threshold value for each user group.

(5) The information processing apparatus according to any one of (2) to (4), wherein the user state detector detects a state of each of the plurality of users based on the sensing data including pulse, perspiration, or brain waves of the plurality of users.

(6) The information processing apparatus according to any one of (2) to (5), wherein the user state detector detects at least one of an excited state, a relaxed state, and an emotional state of the plurality of users based on the sensing data.

(7) The information processing apparatus according to any one of (1) to (6), wherein the user state detector detects a state of each of the plurality of users based on the sensing data obtained by a terminal device carried by each of the plurality of users.

(8) The information processing apparatus according to (7), wherein the user state detector detects a state of each of the plurality of users by using position information obtained by the terminal device as the sensing data.

(9) The information processing apparatus according to (8), wherein the user state detector detects that at least some of the plurality of users are in a congested state with each other based on the position information.

(10) The information processing apparatus according to any one of (7) to (9), wherein the user state detector detects a state of each of the plurality of users based on an operation history of the terminal device.

(11) The information processing apparatus according to any one of (1) to (10), wherein the user state detector detects a state of each of the plurality of users based on the sensing data that is being anonymized.

(12) The information processing apparatus according to any one of (1) to (11), wherein the user state integration unit generates the integrated state information for each user group defined for each area that is set in a space defining the position information.

(13) The information processing apparatus according to (12), wherein the user state integration unit generates the integrated state information for a user group corresponding to an area having a predetermined attribute, from among the areas.

(14) The information processing apparatus according to any one of (1) to (13), wherein the user state integration unit generates the integrated state information for each user having a predetermined attribute from among users included in the user group.

(15) The information processing apparatus according to any one of (1) to (14), wherein the state display generator generates information for displaying an icon that indicates the integrated state information.

(16) The information processing apparatus according to (15), wherein the icon indicates the number of users who are in a predetermined state by means of number, color, or shape.

(17) The information processing apparatus according to (15) or (16), wherein the state display generator generates information for displaying the icon on a map.

(18) The information processing apparatus according to (15) or (16),
wherein the user state integration unit generates the integrated state information for each user group defined for each area that is set in a space defining the position information, and
wherein the state display generator generates information for displaying the icon in a list of the areas.

(19) An information processing method including:
detecting a state of each of a plurality of users based on sensing data provided from the plurality of users together with position information;
integrating the detected state for each user group defined based on the position information to generate integrated state information; and
generating information for displaying the integrated state information in association with a position.

(20) A program for causing a computer to execute:
detecting a state for each of a plurality of users based on sensing data provided from the plurality of users together with position information;
integrating the detected state for each user group defined based on the position information to generate integrated state information; and
generating information for displaying the integrated state information in association with a position.

What is claimed is:

1. An information processing apparatus comprising:
a user state detector configured to detect a state of each of a plurality of users based on sensing data provided from the plurality of users together with position information;
a user state integration unit configured to integrate the detected state for each user group defined based on the position information to generate integrated state information;
and a state display generator configured to generate information for displaying the integrated state information in association with a position,
wherein the user state detector is configured to detect the state of each of the plurality of users by comparing the sensing data with a threshold value, and
wherein the user state detector is configured to set the threshold value, based on the position information, to define each user group.

2. The information processing apparatus according to claim 1, wherein the user state detector is configured to detect the state of each of the plurality of users based on the sensing data including biological information of each of the plurality of users.

3. The information processing apparatus according to claim 2, wherein the user state detector is configured to detect the state of each of the plurality of users by comparing a numerical value of the biological information with the threshold value.

4. The information processing apparatus according to claim 2, wherein the user state detector is configured to detect the state of each of the plurality of users based on the sensing data including pulse, perspiration, or brain waves of the plurality of users.

5. The information processing apparatus according to claim 2, wherein the user state detector is configured to detect at least one of an excited state, a relaxed state, and an emotional state of the plurality of users based on the sensing data.

6. The information processing apparatus according to claim 1, wherein the user state detector is configured to detect the state of each of the plurality of users based on the sensing data obtained by a terminal device carried by each of the plurality of users.

7. The information processing apparatus according to claim 6, wherein the user state detector is configured to detect the state of each of the plurality of users by using the position information obtained by the terminal device as the sensing data.

8. The information processing apparatus according to claim 7, wherein the user state detector is configured to detect that at least some of the plurality of users are in a congested state with each other based on the position information.

9. The information processing apparatus according to claim 6, wherein the user state detector is configured to detect the state of each of the plurality of users based on an operation history of the terminal device, wherein the operation history indicates one or more user operations performed on the terminal device.

10. The information processing apparatus according to claim 1, wherein the user state detector is configured to detect the state of each of the plurality of users based on the sensing data that is being anonymized.

11. The information processing apparatus according to claim 1, wherein the user state integration unit is configured to generate the integrated state information for each user group defined for each area that is set in a space defining the position information.

12. The information processing apparatus according to claim 11, wherein the user state integration unit is configured to generate the integrated state information for a user group corresponding to an area having a predetermined attribute, from among the areas.

13. The information processing apparatus according to claim 1, wherein the user state integration unit is configured to generate the integrated state information for each user having a predetermined attribute from among users included in the user group.

14. The information processing apparatus according to claim 1, wherein the state display generator is configured to generate information for displaying an icon that indicates the integrated state information.

15. The information processing apparatus according to claim 14, wherein the icon indicates the number of users who are in a predetermined state by means of number, color, or shape.

16. The information processing apparatus according to claim 14, wherein the state display generator is configured to generate information for displaying the icon on a map.

17. The information processing apparatus according to claim 14,
wherein the user state integration unit is configured to generate the integrated state information for each user group defined for each area that is set in a space defining the position information, and
wherein the state display generator is configured to generate information for displaying the icon in a list of the areas.

18. An information processing method comprising:
detecting a state of each of a plurality of users based on sensing data provided from the plurality of users together with position information;
integrating the detected state for each user group defined based on the position information to generate integrated state information; and
generating information for displaying the integrated state information in association with a position,
wherein the state of each of the plurality of users is detected by comparing the sensing data with a threshold value, and
wherein the threshold is set, based on the position information, in order to define each user group.

19. A non-transitory computer-readable medium having stored thereon, a set of computer-executable instructions for causing a computer to perform steps comprising:
detecting a state for each of a plurality of users based on sensing data provided from the plurality of users together with position information;
integrating the detected state for each user group defined based on the position information to generate integrated state information; and
generating information for displaying the integrated state information in association with a position,
wherein the state of each of the plurality of users is detected by comparing the sensing data with a threshold value, and
wherein the threshold is set, based on the position information, in order to define each user group.

* * * * *